(12) United States Patent
Olsen

(10) Patent No.: US 6,188,648 B1
(45) Date of Patent: Feb. 13, 2001

(54) DIABETIC CARE OVERVIEW WRISTWATCH

(76) Inventor: Toni L. Olsen, 10189 E. County Rd. B, Lake Nebagamon, WI (US) 54849

( * ) Notice: Under 35 U.S.C. 154(b), the term of this patent shall be extended for 0 days.

(21) Appl. No.: 09/184,991

(22) Filed: Nov. 3, 1998

(51) Int. Cl.$^7$ .................................................. G04B 37/00
(52) U.S. Cl. ............................................. 368/281; 368/10
(58) Field of Search .................................. 368/281, 282, 368/10, 107–113

(56) References Cited

U.S. PATENT DOCUMENTS

| | | |
|---|---|---|
| D. 390,666 | 2/1998 | Lagerlof . |
| 4,151,845 | 5/1979 | Clemens . |
| 4,365,637 | 12/1982 | Johnson . |
| 4,552,464 * | 11/1985 | Rogers .................................. 368/10 |
| 4,575,804 | 3/1986 | Ratcliff . |
| 4,686,624 | 8/1987 | Blum et al. . |
| 4,731,726 | 3/1988 | Allen, III . |
| 4,776,842 | 10/1988 | Franetzki et al. . |
| 4,837,719 | 6/1989 | McIntosh et al. . |
| 4,858,207 | 8/1989 | Buchner . |
| 4,911,256 | 3/1990 | Attikiouzel . |
| 5,012,229 | 4/1991 | Lennon et al. . |
| 5,019,974 | 5/1991 | Beckers . |
| 5,107,469 | 4/1992 | Dodson . |
| 5,216,597 | 6/1993 | Beckers . |
| 5,233,520 | 8/1993 | Kretsch et al. . |
| 5,233,571 | 8/1993 | Wirtschafter . |
| 5,307,263 | 4/1994 | Brown . |
| 5,337,290 | 8/1994 | Ventimiglia et al. . |
| 5,371,687 | 12/1994 | Holmes, II et al. . |
| 5,398,688 | 3/1995 | Laniado . |
| 5,420,108 | 5/1995 | Shohet . |
| 5,542,420 | 8/1996 | Goldman et al. . |
| 5,602,802 | 2/1997 | Leigh-Spencer et al. . |
| 5,628,324 | 5/1997 | Sarbach . |
| 5,672,154 | 9/1997 | Sillen et al. . |
| 5,673,691 | 10/1997 | Abrams et al. . |
| 5,678,571 | 10/1997 | Brown . |
| 5,691,927 | 11/1997 | Gump . |
| 5,691,932 | 11/1997 | Reiner et al. . |
| 5,701,894 | 12/1997 | Cherry et al. . |
| 5,719,780 | 2/1998 | Holmes et al. . |
| 5,729,479 | 3/1998 | Golan . |
| 5,796,640 | 8/1998 | Sugarman et al. . |
| 5,890,128 * | 3/1999 | diaz et al. ................................ 705/2 |

OTHER PUBLICATIONS

"Diabetes At Highest Levels Ever in the U.S.", Doctor's Guide to Medical & Other News, Oct. 30, 1997, HTTP;//www.plsgroup.com/dg/414b2.htm, P/S/L Consulting Group Inc., 1998, 3 pages.

Kiaer, Erik C., "InsuLink (Design Concept)", Children with Diabetes, HTTP://www.childrenwithdiabetes.com/d_06_330.htm, 8 pages.

"GlucoWatch", HTTP;//www.cygn.com/glucowatch.html, 6 pages.

Kroll, Michael I., "New Product for Licensing, Manufacturing, and/or Investors", HTTP;//www.kroll.com/ventimiglia.html, 3 pages.

* cited by examiner

Primary Examiner—Bernard Roskoski
(74) Attorney, Agent, or Firm—Albert W. Watkins

(57) ABSTRACT

A diabetic care overview wristwatch provides a bodily attached watch which incorporates additional functions required for daily diabetes management. A raised numeric keypad encircles a watch face, and minus, equals and clear keys are provided adjacent the watch band. On the display face, a standard time display is provided. A number of additional icons signal various conditions, including low battery, the need for blood glucose testing, the need for insulin injection or oral medication, and a special "thumbs up" signifing proper calculation of carbohydrate counts in diet management. In the event the carbohydrate calculation is improper, a negative carbohydrate count will be displayed. Several alarms are programmable through a depressed key on the side of the watch, and the case is designed to be waterproof. On the back side of the case, the word "diabetic" or other similar legend is imprinted.

20 Claims, 1 Drawing Sheet

DIABETIC CARE OVERVIEW WRISTWATCH

BACKGROUND OF THE INVENTION

1. Field of the Invention

This invention pertains generally to diabetes care and management, and more specifically to a multi-function wristwatch which aids in the management of diabetes.

2. Description of the Related Art

Diabetes describes disease afflicting an estimated sixteen million Americans, and 135 million people world-wide. The disease is characterized by high levels of blood glucose resulting from an inability to produce a sufficient amount or properly use insulin, a hormone necessary for the body to properly convert sugar, starches and other food into a cellular energy source. There are four types of diabetes that are recognized, including: type 1 Insulin Dependent Diabetes Mellitus (IDDM or juvenile diabetes); type 2 Non-Insulin Dependent Diabetes Mellitus (NIDDM or adult onset diabetes); gestational diabetes; and diabetes caused by surgery, drugs, malnutrition, infections, and illnesses.

Complications from diabetes are severe, disabling, and may potentially lead to death. Among the complications are heart disease and stroke, which is the leading cause of diabetes-related deaths, high blood pressure, blindness, kidney disease, nervous system damage, amputations, dental disease, pregnancy complications, diabetic ketoacidosis, and hypersmolar nonketotoic coma. Each of these complications are greatly and adversely influenced by the presence of diabetes. For example, heart disease death rates and risk of stroke are two to four times higher in adults with diabetes than in adults without diabetes. Diabetes is the leading cause of new cases of blindness in adults twenty to seventy-four years in age, and is also the leading cause of end-stage renal disease.

While there is no known cure for diabetes, treatment addresses management of blood glucose levels through dietary control, exercise and medication. The treatment requires a strict regimen that may include of a combination of insulin injections and/or oral medication, multiple daily blood glucose tests, a carefully calculated diet, and planned physical activity. In spite of awareness of the need to follow the regimen, and the seriousness of the consequences of failure to follow it, many diabetics find management to be very difficult at best. In one study of more than 600 diabetes patients, two-thirds agreed that following doctor's recommendations for diabetes care is not easy, and 41 percent indicated that they did not feel successful at managing their diabetes. The largest problem areas identified were related to exercise and diet, which are critical aspects of diabetes care.

According to clinical studies sponsored by the National Institutes of Health, better management would enable people with diabetes to reduce or significantly delay the onset of many of the serious diabetes-related health complications. Nevertheless, and as aforementioned, the management of diabetes has been particularly difficult in those afflicted with the disease. As a result, the annual financial toll has been estimated by the American Diabetes Association at more than $92 billion dollars in the United States in medical expenses, disability and lost wages each year.

Efforts at improving self-management are being made, with significant direct expenditures coming from the United States Congress. In the 1997 Balanced Budget Act, coverage for self-management services provided outside of hospital settings were estimated at a five year amount of $2.1 billion. The goal was to help Medicare beneficiaries better control their blood sugar levels and reduce expensive complication of diabetes. An additional $150 million over five years was targeted to research on type 1 diabetes, with the same amount directed to Indian Health Services for more intensive diabetes prevention and treatment services. Discretionary Health and Human Services spending was set to $345 million for fiscal year 1997 alone. Nevertheless, and in spite of these enormous expenditures, there still remains a serious and unfilled need for a way to provide effective self-management.

There have been a number of devices, systems and methodologies introduced in the prior art. These references and their teachings, as they may pertain to the design and implementation of the present invention, are incorporated herewith. While specific features are discussed hereinbelow, it will be evident that these documents would in various sections not specifically referenced provide a base upon which those of ordinary skill in the art, given the present disclosure, could be directed and guided to implement the present invention, without further undue effort or research. Each of these relevant sections, referenced or otherwise, are considered to be incorporated herein for the purposes of enabling those skilled in the art to make and use the present invention.

In regard to diabetes management systems, U.S. Pat. No. 4,731,726 to Allen, III discloses a checkbook-size portable monitor and management device that includes components for measuring, storing and providing blood glucose values. In addition to the monitoring of blood glucose, a dietary assessment module is provided. Food intake, caloric intake and food exchange are listed as the type of assessment. In U.S. Pat. No. 5,019,974 to Beckers, a hand-held diabetes management device includes features of recording information relating to insulin types and doses, diet, exercise, and other data. Insulin therapy is described, including an audible alarm at a programmed time. Diet therapy is described using one of an exchange system, above/normal/below, or followed/skipped system. A low battery symbol is also provided. There is a brief description of the software, and a reference to the program stored in a 32 KB memory chip. U.S. Pat. No. 5,107,469 to Dodson describes portable reflectance photometer systems having an LCD display and also being able to sound alarm signals to alert diabetics of the need for monitoring glucose levels, receiving an insulin injection, or ingesting requisite food supplements. The device of U.S. Pat. No. 5,307,263 to Brown is primarily directed to children afflicted with diabetes. A Nintendo of America "Game Boy" serves as the hand-held computer, and cartridges are provided to control the device and performed desired functions. Other devices are described as alternatives to the Nintendo Game Boy, including palm top computers and personal appointment calendars. Therein, they state that they provide a self-care blood glucose monitoring system which adapts a hand held microprocessor unit for supplying control signals and signals representative of food intake or other useful information and for displaying information or instruction from a health care professional.

These prior art diabetes management systems fail to provide a convenient way for the entire range of diabetic population to readily manage their care. In particular, these devices are not designed to be body attached nor do they have the simple functioning required by juvenile diabetics and also functioning preferred by older diabetics. Pocket calculator type devices tend to be dropped and broken, misplaced, and lost. In harsher climates, the devices may be destroyed by only a few hours exposure to the elements. A child who wishes to partake in the needed physical activities must set the important management device down and risk forgetting to pick it up again.

In the prior art, there are also watches provided with various physiological monitoring. While these are not generally a part of the present-day diabetes management approach, the teachings incorporated herein by reference to these devices are important to the understandings of the operation and functioning of the present invention, and an appreciation for the novelty therein. In U.S. Pat. No. 4,837,719 to McIntosh et al, a temperature monitor, blood pressure monitor, and pulse rate monitor are combined together with a timer/alarm. In U.S. Pat. No. 5,012,229 to Lennon et al, a wrist watch includes basic heart rate monitoring in conjunction with time keeping and Med-Alert type data. In U.S. Pat. No. 5,602,802 to Leigh-Spencer et al, a portable medication reminder is disclosed as being provided with a hole to facilitate attachment of the module to a separate article regularly carried by the patient, for example, a key ring. A low-battery indication is also provided. In U.S. Pat. No. 5,628,324 to Sarbach a bio-monitoring device may be placed on the handlebar of a bicycle, in the manner most suited to the type of use, and may be combined with time or stopwatch functions. Display means comprise a conventional hour, minute and second display, and a special display of the parameters measured by the processing device. The display may also comprise flags and symbols corresponding to parameters to be displayed or to certain special circumstances, for example the end of the batteries' life. The watch also comprises push buttons enabling different functions to be called. In U.S. Pat. No. 5,691,932 to Reiner et al, a care-giver data collection and reminder system includes schedules to remind the care giver of medication times, feedings, etc. Icons are provided to assist in international use and to simplify the operation of the device. Alarms can be initiated by the micro-controller and can either be a display device or auditory. The apparatus includes a carrying case that allow the operator to attach the device on a changing table, to their belt, refrigerator, or to carry it around the neck or wrist. In U.S. Pat. No. 5,719,780 to Holmes and Moe, a medication reminder takes a wrist watch configuration, and also includes a low battery indicator. The device may be placed in a pill box, or may be worn around the neck or provided on a key chain.

In the area of diet management, U.S. Pat. No. 5,542,420 to Goldman et al discloses a diet management system implemented in a notebook PC or similar device. Included with the diet management is the requirement for pharmaceuticals and carbohydrates. U.S. Pat. No. 4,911,256 by Attikiouzel and U.S. Pat. No. 5,233,520 by Kretsch et al each disclose "smart scales" that are programmed to help with dietary management, and U.S. Pat. No. 5,691,927 to Gump discloses a hand-held food pyramid diet calculator.

Additional patents that are incorporated herein for their more general teachings of related programming and hardware and software implementation are U.S. Pat. No. 4,858,207 by Buchner, U.S. Pat. No. 5,233,571 by Wirtschafter, U.S. Pat. No. 5,371,687 by Holmes, II et al, U.S. Pat. No. 5,678,571 by Brown, U.S. Pat. No. 5,701,894 to Cherry et al, and U.S. Pat. No. Des. 390,666 to Lagerloff.

SUMMARY OF THE INVENTION

In a first manifestation of the invention, a combined wristwatch and diabetes management device comprises a numeric keypad including a separate key for each of the ten decimal digits; a time keeper for generating time and alarm signals; a means for generating a first alarm signal responsive to the time keeper arriving at a first predetermined time, indicating a need for blood glucose testing; a means for generating a second alarm signal responsive to the time keeper arriving at a second predetermined time, indicating a need for medication; a means for generating a third alarm signal responsive to the time keeper arriving at a third predetermined time, indicating carbohydrates that should be consumed and requesting input about the carbohydrates intended to be immediately consumed; a means for calculating a difference between carbohydrates that should be consumed and carbohydrates intended to be immediately consumed; signalling means to positively signal when carbohydrates intended to be immediately consumed equals carbohydrates that should be consumed; and signalling means to negatively signal when carbohydrates intended to be immediately consumed are greater than carbohydrates that should be consumed.

In a second manifestation, the invention comprises a method for managing diabetes including the steps of: bodily strapping a microprocessor-controlled time keeper to a diabetic patient; setting a first alarm which indicates the need for medication at a predetermined first time; activating the first alarm at the predetermined first time; setting a second alarm which indicates the need for carbohydrate consumption, including the number of carbohydrates required; activating the second alarm at the predetermined second time; setting a third alarm which indicates the need for blood glucose testing; activating the third alarm at the predetermined third time; entering an amount of carbohydrates consumed responsive to the second alarm; generating a positive signal if the amount of carbohydrates entered is within a predetermined desirable range; and generating a negative signal if the amount of carbohydrates entered is greater than the predetermined desirable range.

In a third manifestation of the invention, a wrist watch has calculation functions and special purpose icons for diabetes management, including a wrist band for wrapping about a human forearm; a watch face having an alpha-numeric display thereon for displaying time and carbohydrate count back; a first icon representative of a need for blood glucose testing; a second icon representative of a need for medication; a third icon representative of proper carbohydrate consumption; ten decimal keys surrounding the alpha-numeric display, each representative of a unique decimal between and including zero and nine; three keys adjacent the decimal keys and wrist band representative of clear, minus and equal calculator functions; and a recessed setting button on an edge of the watch normal to the watch face.

Various other features are provided for within each of the individual manifestations.

OBJECTS OF THE INVENTION

A first object of the invention is the provision of a convenient bodily-attached diabetes management system. A second object is that the device be operable by as wide a range of people afflicted with diabetes as possible, and particularly to include both juveniles and the elderly. A third object is the provision of a device that is as safe and reliable as practical. A further object of the invention is the provision of a device which may be readily manufactured using current production techniques and existing materials, to thereby allow for delivery of the device in large quantity and at reasonable cost. Another object of the invention is the provision of a small and compact device which will be worn by users without hesitation and may be worn throughout the day and night, thereby minimizing the chance of destruction or loss of the device. Yet a further object of the invention is the provision of a simple carbohydrate count back monitoring system which requires very little time for implementation by the user, thereby reducing the complexity of the device and the burden for usage. These and other objects of the invention are addressed by the preferred embodiment of the present invention.

DESCRIPTION OF THE PREFERRED EMBODIMENT

Figure 1:
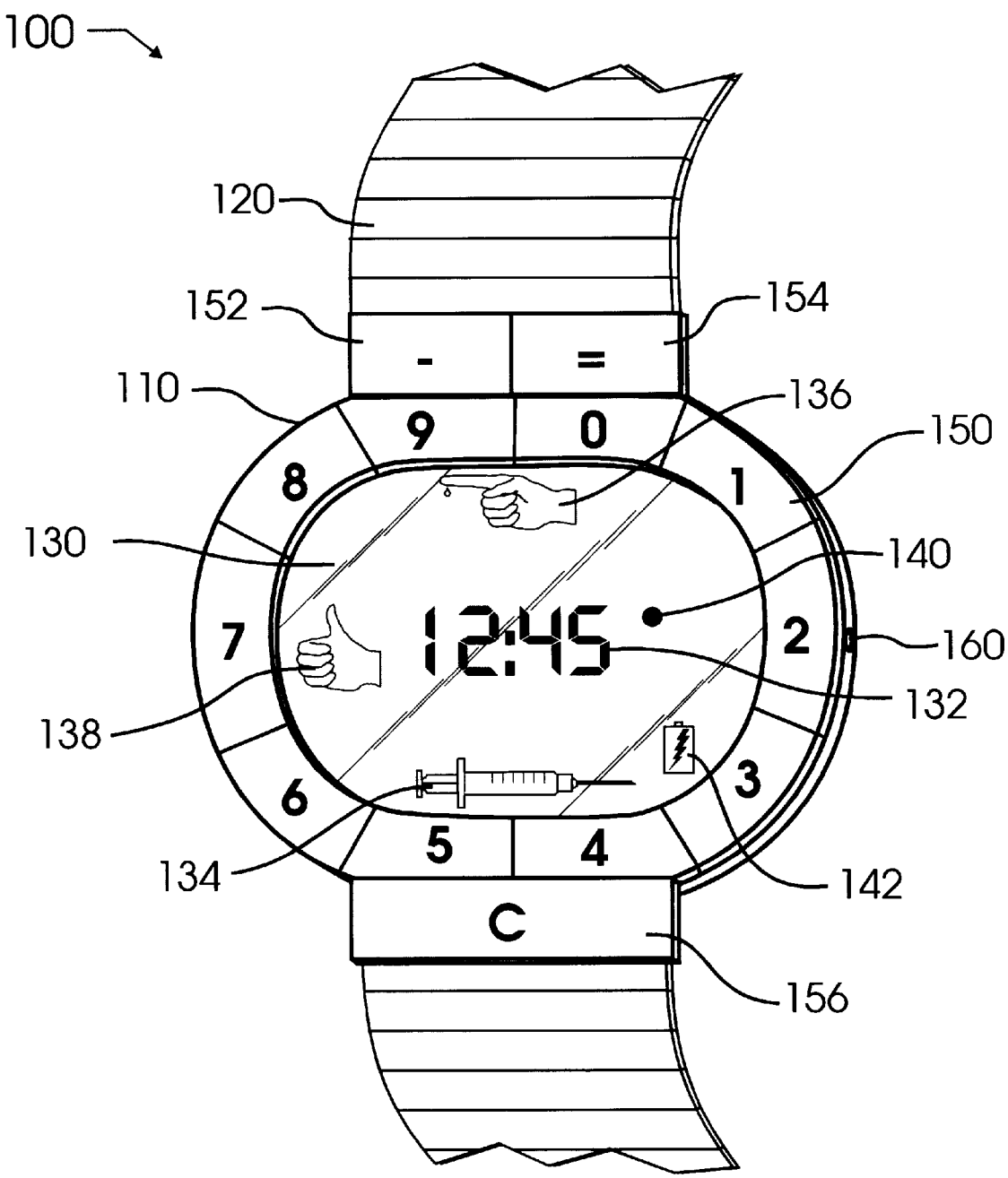
FIG. 1 illustrates the preferred embodiment of the invention from a projected view.

In the preferred embodiment, the diabetes management device 100 includes a watch body 110 which may be attached to a person by watch band 120. Watch body 110 further comprises a face 130 which might comprise a glass-covered liquid crystal display as is known in the prior art, or may alternatively be one of a variety of other known display types. On face 130 there will be provided a digital time display 132 as is known in the prior art, which might, for example, include a small p.m. indicator 140. For the purposes of the preferred embodiment, a dot has been used at 140, but those in the watch art will recognize that any of a variety of known indicator symbols are available, and may, for example, include a small "A" or "P" or other such form. In addition to the basic time function, diabetes management device 100 also includes a full numeric keypad 150 encircling face 130, and slightly elevated therefrom. Each digit from zero through nine is provided to enable the user to easily enter any desired number combination. A minus key 152, equals key 154 and clear key 156 are also provided adjacent to keypad 150 and also adjacent to watch band 120, preferably in the region of attachment of band 120 to body 110. By keeping these keys in a circle about watch face 130, the difficulty of pressing a proper key is reduced, since there are only two adjacent keys, as opposed to the four of a regular calculator-type watch keypad. This is most beneficial for the smaller children and elderly, though more convenient for all persons using the watch.

Each of the keys 150 are elevated to provide easy access for use. A small, preferably recessed button 160 may be used to perform various time and alarm setting functions, and more than one such button may be provided. Several special icons are also provided on face 130, including syringe icon 134, blood glucose icon 136, thumbs-up icon 138, and low battery icon 142. Low battery icon 142 may alternatively be an icon signalling either watch malfunction or impending malfunction, or such feature may be provided for separately. The icons illustrated are preferred, though one of ordinary skill in the art will understand that other suitable icons or indicators may be selected.

Though not specifically illustrated, the watch is preferably assembled using known watch assembly materials and techniques to be waterproof and durable. A back light is provided for easy viewing at night or in a dimly lit environment. An imprint may also be provided somewhere on the watch which identifies the wearer as diabetic, such as on the back casing of the watch. Over a period of time, the preferred embodiment will then be recognizable by the medical community as a medical identification.

The preferred diabetes management device 100 is provided through software with a total of eight alarm settings, though once again more or fewer settings may be provided. Eight is a comfortable number to accommodate most users, while keeping cost and complexity of the watch to a minimum. These different settings may be for alarm function only, or a person may program one or more of the icons 134–138 to appear with each alarm setting. This may be achieved by one of various techniques known in the art, such as pressing and holding alarm button 160 for an appropriate amount of time while device 100 cycles through each possible combination, pressing button 160 multiple times to manually sequence through the various icons, or selection of one or more numeric buttons to activate one or more of the icons.

As is known in the art, various activities are desirably set to occur at particular times each day. By appropriate programming of the alarms, at the appropriate times management device 100 may be used to signal a necessary activity. For example, a 6:30 a.m. alarm might be programmed to signal the need for both a blood sugar test and insulin injection. For this particular alarm, both icons 134 and 136 should be activated, and an accompanying audio alarm will chime. A silent alarm may be used, as are known in the art of paging devices, though the chime is preferred. At 6:45 a.m., a carbohydrate countdown may be required. The alarm will sound, and the alpha-numeric display 132 will read "60" or "60 Gm", indicating the initial carbohydrate count. The individual wearing device 100 will then enter a minus by touching key 152 and then the actual number of carbohydrates which have been eaten or selected, followed by the equal key 154. For the present example, if a thirty is entered with this 6:45 alarm, thirty will be subtracted and thirty carbohydrates will remain. If the entry is appropriate, the thumbs-up icon 138 will display and, optionally, an up-beat chime or tune may be played. At 9:00 a.m., the alarm is set to sound again, and, at this time, it will indicate "30" or "30 Gm". Once again, the wearer will be expected to enter the appropriate amount. If the wearer enters more than appropriate, for example in this instance 45, the display will show a negative 15 and the watch light will preferably flash This is an optional feature for all icons. At this point, management device 100 has preformed the intended function of advising the wearer of the appropriate amounts of carbohydrates and whether those amounts have been met. The wearer then must make the final decision whether to proceed to consume more carbohydrates than desired. The wearer will need to press the clear key to initiate a return to regular time display after device 100 displays either the negative carb amount or thumbs-up icon 138. The carbohydrate count back is required to be completed each time after the sounding of the alarm to allow the watch to return to time display. This measure has been provided for to help prevent hypoglycemia, by requiring the user to enter a count back amount thereby suggesting carbohydrate intake.

The capability of the preferred embodiment for calculating carbohydrates only provides for subtracting carbohydrates. This is done with the intent for use by all ages. In particular with children and the elderly, there is no opportunity that a plus key will be mistakenly selected, which might otherwise cause an incorrect intake of carbohydrates. As is known, too many carbohydrates can potentially lead to hyperglycemia. In addition, the absence of the plus key saves precious space on the watch.

Because the watch is programmable, the user or a physician, dietician, parent or other concerned party is able to enter alarm times and carbohydrate amounts to meet the user's needs. These needs can then be maintained as established by the responsible physician or dietician. By combining the important features of time keeping and visual and audible alarms together with carbohydrate count back into an easy-to-use and hard-to-lose wrist watch, the primary objectives of the present invention are met.

While the foregoing details what is felt to be the preferred embodiment of the invention, no material limitations to the scope of the claimed invention are intended. Further, features and design alternatives that would be obvious to one of ordinary skill in the art are considered to be incorporated herein. A number of alternative features, constructions and functionalities will be obvious to those of ordinary skill when the present disclosure is considered in conjunction with the prior art referenced herein. The scope of the invention is set forth and particularly described in the claims hereinbelow.

I claim:

1. A combined wristwatch and diabetes management device comprising:
   a numeric keypad including a separate key for each of the ten decimal digits;
   a time keeper means for generating time and alarm signals;
   a means for generating a first alarm signal responsive to said time keeper means arriving at a first predetermined time, indicating a need for blood glucose testing;
   a means for generating a second alarm signal responsive to said time keeper means arriving at a second predetermined time, indicating a need for medication;
   a means for generating a third alarm signal responsive to said time keeper means arriving at a third predetermined time, indicating carbohydrates that should be consumed and requesting input to said combined wristwatch and diabetes management device the carbohydrates intended to be immediately consumed;
   a means for calculating a difference between said carbohydrates that should be consumed and said carbohydrates intended to be immediately consumed;
   signalling means to positively signal when said carbohydrates intended to be immediately consumed equals said carbohydrates that should be consumed; and
   signalling means to negatively signal when said carbohydrates intended to be immediately consumed is greater than said carbohydrates that should be consumed.

2. The combined wristwatch and diabetes management device of claim 1 further comprising a means for generating a fourth alarm signal indicating potential device malfunction.

3. The combined wristwatch and diabetes management device of claim 1 further comprising a wrist band for wrapping about a human forearm.

4. The combined wristwatch and diabetes management device of claim 1 further comprising a face plate having an alpha-numeric display means.

5. The combined wristwatch and diabetes management device of claim 4 wherein said numeric keypad is elevated from and surrounds said face plate.

6. The combined wristwatch and diabetes management device of claim 4 wherein said alphanumeric display means further comprises a liquid crystal display.

7. The combined wristwatch and diabetes management device of claim 4 further comprising icons for signalling said first, second and third alarms.

8. The combined wristwatch and diabetes management device of claim 1 further comprising a waterproof housing about said time keeper.

9. The combined wristwatch and diabetes management device of claim 1 further comprising a recessed means for setting times of said first, second and third alarms.

10. A method for managing diabetes comprising the steps of:
    bodily strapping a microprocessor-controlled time keeper to a diabetic patient;
    setting a first alarm of said time keeper which indicates the need for medication at a predetermined first time;
    activating said first alarm at said predetermined first time;
    setting a second alarm of said time keeper which indicates the need for carbohydrate consumption, including the number of carbohydrates required;
    activating said second alarm at said predetermined second time;
    setting a third alarm of said time keeper which indicates the need for blood glucose testing;
    activating said third alarm at said predetermined third time;
    entering an amount of carbohydrates consumed responsive to said second alarm;
    generating a positive signal if said amount of carbohydrates entered is within a predetermined desirable range; and
    generating a negative signal if said amount of carbohydrates entered is greater than said predetermined desirable range.

11. The method for managing diabetes of claim 10 wherein the step of generating said negative signal comprises flashing a light and displaying a difference between said amount of carbohydrates entered and said predetermined desirable range.

12. The method for managing diabetes of claim 10 wherein the step of generating a positive signal comprises playing an up-beat tune and displaying an icon on a display of said time keeper indicative of a positive entry.

13. The method for managing diabetes of claim 10 comprising the additional step of displaying the time of day.

14. The method for managing diabetes of claim 13 wherein the steps of entering and generating occur after a first step of displaying, and prior to returning to said displaying step.

15. A compact and unobtrusive wrist watch having calculation functions and special purpose icons for diabetes management, comprising:
    a watch face having an alpha-numeric display thereon for displaying time and carbohydrate count back;
    a wrist band for wrapping about a human forearm;
    first and second connectors for connecting said wrist band to said watch face;
    a first signal uniquely representative of a need for blood glucose testing;
    a second signal uniquely representative of a need for medication;
    a third signal uniquely representative of proper carbohydrate consumption;
    ten decimal keys adjacent said alpha-numeric display, each representative of a unique decimal between and including zero and nine;
    three keys representative of clear, minus and equal calculator functions located over at least one of said first and second connectors; and
    a recessed setting button on an edge of said watch normal to said watch face.

16. The wrist watch of claim 15 further comprising a potential watch malfunction.

17. The wrist watch of claim 16 wherein said potential watch malfunction is a low battery condition.

18. The wrist watch of claim 15 wherein said ten decimal keys surround said alpha-numeric display.

19. The wrist watch of claim 15 further comprising a watch casing having a legend imprinted thereon associating a wearer with diabetes.

20. The wrist watch of claim 15 wherein said first, second and third signals are icons.

* * * * *